United States Patent [19]

Borzatta et al.

[11] Patent Number: 5,496,875

[45] Date of Patent: Mar. 5, 1996

[54] DERIVATIVES OF 2,2,6,6-TETRAMETHYL-4-PIPERIDINOL FOR USE AS LIGHT STABILIZERS, HEAT STABILIZERS AND OXIDATION STABILIZERS FOR ORGANIC MATERIALS

[75] Inventors: Valerio Borzatta; Roberto Scrima, both of Bologna; Primo Carrozza, Verona, all of Italy

[73] Assignee: Ciba-Geigy Corporation, Tarrytown, N.Y.

[21] Appl. No.: 273,575

[22] Filed: Jul. 11, 1994

[30] Foreign Application Priority Data

Jul. 16, 1993 [IT] Italy ................ MI93A001582

[51] Int. Cl.⁶ .................................... C08K 5/34
[52] U.S. Cl. .................... 524/99; 252/403; 546/192; 546/216; 546/217; 546/242
[58] Field of Search ............... 252/403; 524/99; 546/192, 216, 217, 242

[56] References Cited

U.S. PATENT DOCUMENTS

| | | | |
|---|---|---|---|
| 3,640,928 | 2/1972 | Murayama et al. | 260/23 |
| 3,840,494 | 10/1974 | Murayama et al. | 260/45.8 |
| 3,984,371 | 10/1976 | Murayama et al. | 260/45.75 |
| 4,021,432 | 5/1977 | Holt et al. | 260/293.64 |
| 4,089,842 | 5/1978 | Ramey et al. | 524/99 |
| 4,101,508 | 7/1978 | Minagawa et al. | 524/99 |
| 4,115,476 | 9/1978 | Minagawa et al. | 260/880 |
| 4,405,737 | 9/1983 | Hirai et al. | 524/99 |
| 4,419,472 | 12/1983 | Berner et al. | 524/102 |
| 4,618,634 | 10/1986 | Cantatore et al. | 524/99 |
| 4,668,722 | 5/1987 | Mack | 524/99 |
| 4,670,489 | 6/1987 | Takahashi et al. | 524/99 |
| 5,028,645 | 7/1991 | Gugumus et al. | 524/102 |
| 5,204,473 | 4/1993 | Winter et al. | 546/188 |
| 5,300,545 | 4/1994 | Kazmierczak et al. | 524/99 |

FOREIGN PATENT DOCUMENTS

| | | |
|---|---|---|
| 243319 | 10/1987 | European Pat. Off. . |
| 518807 | 12/1992 | European Pat. Off. . |
| 2352606 | 5/1974 | Germany . |
| 4242916 | 1/1994 | Germany . |
| 177380 | 1/1992 | Taiwan . |
| 181287 | 4/1992 | Taiwan . |
| 189279 | 8/1992 | Taiwan . |
| 1466628 | 3/1977 | United Kingdom . |
| 1490485 | 11/1977 | United Kingdom . |
| 2106901 | 4/1983 | United Kingdom . |
| 8901474 | 2/1989 | WIPO . |
| 9315063 | 8/1993 | WIPO . |

OTHER PUBLICATIONS

R. Gachter and H. Muller; Plastics Additives Handbook, pp. 138–141 (1983).
Pat. Abst. of Japan (11) 60–188959(A).
Chem. Abstr. vol. 104, No. 139273.
Chem. Abstr. vol. 96, No. 200751.
Polymer International, 1994, vol. 34 pp. 443–447.
Research Disclosure 1986, vol. 263, pp. 166–169 No. 26373.
Research Disclosure—No. 314, Jun. 1990 pp. 474–480.
C.A 111:98399v.
Derwent Abst. 89–025378/04.
CA 104:177575h, Van Maele et al., Res. Discl. 1986, 263, 166–9.

*Primary Examiner*—Kriellion S. Morgan
*Attorney, Agent, or Firm*—Luther A. R. Hall; Michele A. Kovaleski

[57] ABSTRACT

The present invention relates to novel piperidine compounds of the formula (I)

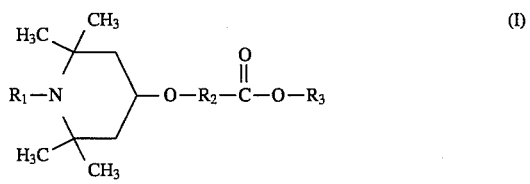

in which $R_1$, $R_2$ and $R_3$ are as defined in the text.

The compounds of the invention can be used as light stabilizers, heat stabilizers and oxidation stabilizers for organic materials, in particular synthetic polymers.

12 Claims, No Drawings

DERIVATIVES OF 2,2,6,6-TETRAMETHYL-4-PIPERIDINOL FOR USE AS LIGHT STABILIZERS, HEAT STABILIZERS AND OXIDATION STABILIZERS FOR ORGANIC MATERIALS

The present invention relates to novel piperidine compounds, to their use as light stabilizers, heat stabilizers and oxidation stabilizers for organic materials, in particular synthetic polymers, and to organic materials thus stabilized.

Numerous patents on the preparation of 2,2,6,6-tetramethyl-4-piperidinol derivatives and the use thereof as stabilizers for synthetic polymers have been published, in particular U.S. Pat. No. 3,640,928, U.S. Pat. No. 3,840,494, U.S. Pat. No. 4,021,432, U.S. Pat. No. 4,101,508, U.S. Pat. No. 4,115,476 and U.S. Pat. No. 4,419,472, GB-A-1 466 628, GB-A-1 490 485, GB-A-2 106 901 EP-A-243 319, EP-A-300 160 and EP-A-518 807.

The present invention relates to novel compounds of the formula (I)

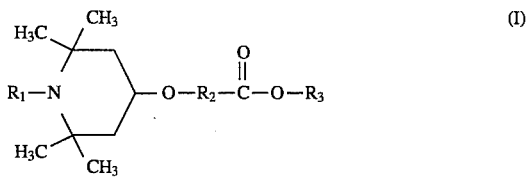

in which $R_1$ is hydrogen, $C_1$–$C_8$alkyl, O·, OH, $CH_2CN$, $C_1$–$C_{18}$alkoxy, $C_5$–$C_{12}$cycloalkoxy, $C_3$–$C_6$alkenyl, $C_7$–$C_9$phenylalkyl unsubstituted or mono-, di- or tri-substituted on the phenyl by $C_1$–$C_4$alkyl; or aliphatic $C_1$–$C_8$acyl, $R_2$ is a direct bond, methylene, carbonyl or a group

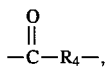

the group $R_4$ being bound to the group

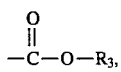

$R_3$ is $C_5$–$C_{18}$alkyl, $C_3$–$C_{18}$alkenyl, $C_5$–$C_{12}$ cycloalkyl unsubstituted or mono-, di-or tri-substituted by $C_1$–$C_4$alkyl; or $C_7$–$C_9$phenylalkyl unsubstituted or mono-, di- or tri-substituted on the phenyl by $C_1$–$C_4$alkyl, $R_4$ is linear $C_1$–$C_4$alkylene, a group

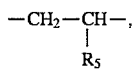

a group

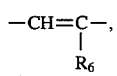

$C_2$–$C_4$oxaalkylene, $C_5$–$C_7$cycloalkyl-1,2-ene, $C_5$–$C_7$cycloalken-1,2-ylene or 1,2-phenylene, $R_5$ is $C_1$–$C_{18}$alkyl or $C_3$–$C_{18}$alkenyl, and $R_6$ is hydrogen or $C_1$–$C_4$alkyl.

Examples of alkyl having not more than 18 carbon atoms are methyl, ethyl, propyl, isopropyl, butyl, 2-butyl, t-butyl, pentyl, 2-pentyl, isopentyl, hexyl, heptyl, octyl, 2-ethylhexyl, t-octyl, nonyl, decyl, undecyl, dodecyl, tridecyl, tetradecyl, hexadecyl and octadecyl.

Examples of $C_1$–$C_{18}$alkoxy $R_1$ are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. Preferred examples are $C_6$–$C_{12}$alkoxy, in particular heptoxy and octoxy.

Examples of $C_5$–$C_{12}$cycloalkyl $R_3$ unsubstituted or mono-, di- or tri-substituted by $C_1$–$C_4$alkyl are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl and cyclododecyl. Unsubstituted or substituted cyclohexyl is preferred.

Examples of $C_5$–$C_{12}$cycloalkoxy $R_1$ are cyclopentoxy, cyclohexoxy, cycloheptoxy, cyclooctoxy, cyclodecyloxy and cyclododecyloxy. Cyclopentoxy and cyclohexoxy are preferred.

Examples of alkenyl having not more than 18 carbon atoms are allyl, 2-methylallyl, butenyl, hexenyl, octenyl, decenyl, undecenyl, dodecenyl, tetradecenyl, hexadecenyl and octadecenyl.

Those alkenyls are preferred in which the carbon atom in the 1-position is saturated.

Examples of $C_7$–$C_9$phenylalkyl unsubstituted or mono-, di- or tri-substituted on the phenyl by $C_1$–$C_4$alkyl are benzyl, methylbenzyl, dimethylbenzyl, trimethylbenzyl and 2-phenylethyl. Benzyl is preferred.

Representative examples of aliphatic acyl $R_1$ having not more than 8 carbon atoms are acetyl, propionyl, butyryl, isobutyryl, pentanoyl, hexanoyl, heptanoyl, octanoyl, acryloyl and crotonyl. $C_1$–$C_8$Alkanoyl and $C_3$–$C_8$alkenoyl are particularly preferred.

Linear $C_1$–$C_4$alkylene $R_4$ can be methylene, ethylene, trimethylene and tetramethylene.

$C_2$–$C_4$Oxaalkylene $R_4$ can, for example, be 2-oxa-1,3-propanediyl or 3-oxa-1,5-pentanediyl.

$C_5$–$C_7$Cycloalkyl-1,2-ene or $C_5$–$C_7$cycloalken-1,2-ylene $R_4$ is, for example, 1,2-cyclohexylene, 4-methyl-1,2-cyclohexylene, 4-cyclohexen-1,2-ylene or 4-methyl-4-cyclohexen-1,2ylene.

Preferred definitions of $R_1$ are hydrogen, $C_1$–$C_4$alkyl, OH, $C_6$–$C_{12}$alkoxy, $C_5$–$C_8$ cycloalkoxy, allyl, benzyl or acetyl, in particular hydrogen or methyl.

Those compounds of the formula (I) are preferred in which $R_2$ is a direct bond, methylene, carbonyl, a group

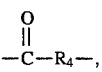

$R_3$ is $C_5$–$C_{18}$alkyl, $C_5$–$C_{18}$alkenyl, $C_5$–$C_8$cycloalkyl unsubstituted or mono-, di-or tri-substituted by $C_1$–$C_4$alkyl; or benzyl unsubstituted or mono-, di- or tri-substituted on the phenyl by $C_1$–$C_4$alkyl, $R_4$ is linear $C_1$–$C_3$alkylene, a group

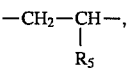

a group

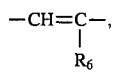

$C_2$–$C_4$oxaalkylene, $C_6$–$C_7$cycloalkyl-1,2-ene, $C_6$–$C_7$cycloalken-1,2-ylene or 1,2-phenylene, $R_5$ is methyl, $C_3$–$C_{18}$alkyl or $C_3$–$C_{18}$alkenyl, and $R_6$ is hydrogen or $C_1$–$C_2$alkyl.

Those compounds of the formula (I) are particularly preferred in which $R_2$ is a direct bond, methylene, carbonyl or a group

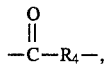

$R_3$ is $C_6$–$C_{18}$alkyl, $C_6$–$C_{18}$alkenyl, cyclohexyl unsubstituted or mono-, di- or tri-substituted by $C_1$–$C_4$alkyl; or benzyl unsubstituted or mono-, di- or tri-substituted on the phenyl by $C_1$–$C_4$alkyl, $R_4$ is ethylene, trimethylene, a group

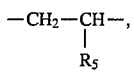

a group

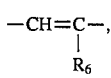

a group —$CH_2$—O—$CH_2$—, 1,2-cyclohexylene, 4-methyl-1,2-cyclohexylene, 4-cyclohexen-1,2-ylene, 4-methyl-4-cyclohexen-1,2-ylene or 1,2-phenylene, $R_5$ is methyl, $C_4$–$C_{18}$alkyl or $C_4$–$C_{18}$alkenyl, and $R_6$ is hydrogen or methyl.

Those compounds of the formula (I) are of special interest in which $R_2$ is a direct bond, methylene or a group

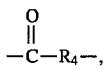

$R_3$ is $C_8$–$C_{18}$alkyl, undecenyl, octadecenyl, cyclohexyl or benzyl, $R_4$ is ethylene, trimethylene, a group

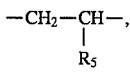

a group —CH=CH—, a group —$CH_2$—O—$CH_2$—, 1,2-cyclohexylene or 4-methyl-1,2-cyclohexylene, and $R_5$ is methyl, $C_4$–$C_{12}$alkyl or $C_4$–$C_{12}$alkenyl.

Those compounds of the formula (I) are of particular interest in which $R_1$ is hydrogen or methyl, $R_2$ is a direct bond or a group

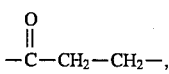

and $R_3$ is $C_8$–$C_{18}$alkyl.

The compounds of the present invention can be prepared by reacting a compound of the formula (II)

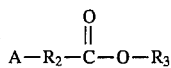

where A is Cl or Br, with a piperidinol of the formula (III)

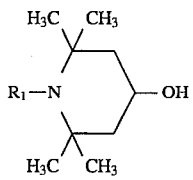

neutralizing the hydrohalic acid released with a preferably inorganic base, for example sodium, potassium or calcium hydroxide or carbonate, or by reacting a compound of the formula (II) with a compound of the formula (IV)

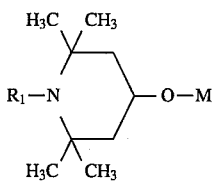

where M is Li, Na or K.

If $R_2$ is a group

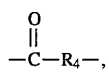

the compounds of the formula (I) are preferably prepared by reacting a piperidinol of the formula (III) with an anhydride of the formula (V)

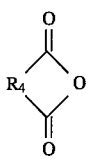

to obtain a half-ester of the formula (VI)

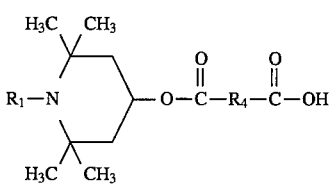

which is subsequently reacted with a compound of the formula (VII)

$R_3$—A (VII)

with A being as defined above, in the presence of an organic base, for example triethylamine or tributylamine, or by reacting a compound of the formula (VII) with a compound of the formula (VIII)

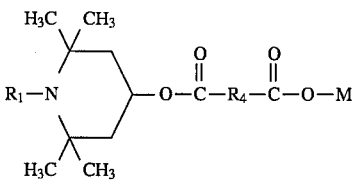

with M being as defined above.

The various reactions can be effected in an inert organic solvent, for example toluene, xylene, dioxane, tetrahydrofuran, dimethylformamide, N,N-dimethylacetamide or N-methyl- 2-pyrrolidinone, operating at a temperature from −20° C. to 180° C., preferably from −10° C. to 150° C.

The piperidinols of the formula (III) are prepared by catalytic reduction of the corresponding 4-piperidinones or by introducing, using the appropriate reagents, the group $R_1$ (for $R_1 \neq H$) in the position 1 of the 2,2,6,6-tetramethyl-4-piperidinol.

As mentioned at the outset, the compounds of the present invention are highly effective in improving the light stability, heat stability and oxidation stability of organic materials, in particular synthetic polymers and copolymers.

Examples of such organic materials which can be stabilized are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), polyα-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

The compounds of the formula (I) are particularly suitable for improving the light stability, heat stability and oxidation stability of polyolefins, especially polyethylene and polypropylene.

The invention also relates to compositions comprising an organic material that is susceptible to degradation induced by light, heat and/or oxidation and at least one compound of formula (I).

The compounds of the formula (I) can be used in mixtures with organic materials in various proportions depending on the nature of the material to be stabilized, on the end use and on the presence of other additives.

In general, it is appropriate to use, for example, 0.01 to 5% by weight of the compounds of the formula (I), relative to the weight of the material to be stabilized, preferably between 0.05 and 1%.

In general, the compounds of the formula (I) can be added to the polymeric materials before, during or after the polymerization or crosslinking of the said materials.

The compounds of the formula (I) can be incorporated in the polymeric materials in the pure form or encapsulated in waxes, oils or polymers.

The compounds of the formula (I) can be incorporated in the polymeric materials by various processes, such as dry mixing in the form of powder, or wet mixing in the form of solutions or suspensions or also in the form of a masterbatch; in such operations, the polymer can be used in the form of powder, granules, solutions, suspensions or in the form of latices.

The materials stabilized with the products of the formula (I) can be used for the production of mouldings, films, tapes, monofilaments, fibres, surface coatings and the like.

If desired, other conventional additives for synthetic polymers, such as antioxidants, UV absorbers, nickel stabilizers, pigments, fillers, plasticizers, antistatic agents, flameproofing agents, lubricants, corrosion inhibitors and metal deactivators, can be added to the mixtures of the compounds of the formula (I) with the organic materials.

Particular examples of additives which can be used in admixture with the compounds of the formula (I) are:

1. Antioxidants
   1.1. Alkylated monophenols, for example 2,6-di-tert-butyl-4-methylphenol, 2-tert-butyl- 4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-di-nonyl-4-methylphenol, 2,4- dimethyl-6 -(1'-methylundec-1'-yl)phenol, 2,4-dimethyl-6-(1'-methylheptadec-1'-yl)phenol, 2,4-dimethyl- 6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl- 4-nononylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl- 4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-ten-butyl-4-methylphenol), 2,2'-thiobis(4-octylphenol), 4,4'-thiobis(6-tert-butyl-3-methylphenol), 4,4'-thiobis( 6-tert-butyl-2-methylphenol), 4,4'-thiobis-(3,6-di-sec-amylphenol), 4,4'-bis-(2,6-dimethyl- 4-hydroxyphenyl) disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis [4-methyl-6-(α -methylcyclohexyl)phenol], 2,2'-methylenebis(4-methyl-6-cyclohexylphenol), 2,2'-methylenebis( 6-nonyl-4-methylphenol), 2,2'-methylenebis(4,6-di-tert-butylphenol), 2,2'-ethylidenebis( 4,6-di-tert-butylphenol), 2,2'-ethylidenebis(6-tert-butyl-4-isobutylphenol), 2,2'-methylenebis[ 6-(α-methylbenzyl)-4-nonylphenol], 2,2'-methylenebis[6-(α,α-dimethylbenzyl)- 4-nonylphenol], 4,4'-methylenebis(2,6-di-tert-butylphenol), 4,4'-methylenebis(6-tert-butyl- 2-methylphenol), 1,1-bis(5-tert-butyl-4-hydroxy-2-methylphenyl)butane, 2,6-bis(3-tert-butyl- 5-methyl-2-hydroxybenzyl)-4-methylphenol, 1,1,3-tris(5-tert-butyl-4-hydroxy- 2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl- 4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl- 4-hydroxy2-methylphenyl)-4-n-dodecylmercaptobutane, 1,1,5,5-tetra-(5-tert-butyl- 4-hydroxy2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tris-(3,5-di-tert-butyl- 4-hydroxybenzyl)amine, bis(4-tert-butyl-3-hydroxy-2,6-dimethylbenzyl )dithioterephthalate, bis(3,5-di-tert-butyl-4-hydroxybenzyl)sulfide, isooctyl-3,5di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-ten-butyl-4-hydroxybenzyl)malonate, bis[ 4-(1, 1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)- 2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)- 1,3,5-triazine, 2-octylmercapto-4,6-bis(3,5-di-tert-butyl-4-hydroxyanilino)- 1,3,5-triazine, 2-octylmercapto-4,6-bis(3,5-di-tert-butyl-4-hydroxyphenoxy) 1,3,5-triazine, 2,4,6-tris(3,5-di-tert-butyl-4-hydroxyphenoxy)-1,2,3-triazine, 1,3,5-tris( 3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl- 4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert, butyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4,hydroxy-3-methylphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl)propionic acid e.g. N,N'-bis(3,5-di-tert-butyl- 4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl- 2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl- 2'-hydroxy-5'-methylphenyl)-5-chloro-benzotriazole, 2-(3'-sec-butyl- 5'-tert-butyl-2'-hydroxyphenyl)benzotriazole, 2-(2'-hydroxy-4'-octyloxyphenyl)benzotriazole, 2-( 3',5'-di-tert-amyl-2'-hydroxyphenyl)benzotriazole, 2-(3',5'-bis-(α,α-dimethylbenzyl)-2' -hydroxyphenyl)benzotriazole, mixture of 2-(3'-tert-butyl-2'-hydroxy-5'-(2-octyloxycarbonylethyl)phenyl)- 5-chloro-benzotriazole, 2-(3'-tert-butyl-5'-[2-(2-ethylhexyloxy)-carbonylethyl] -2'-hydroxyphenyl)-5-chloro-benzotriazole, 2-(3'-tert-butyl-2'-hydroxy- 5'-(2-methoxycarbonylethyl)phenyl)-5-chloro-benzotriazole, 2-(3'-tert-butyl-2'-hydroxy-5'-(2 -methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl] -2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl] -2H-benzotriazole with polyethylene glycol 300; [R—CH$_2$CH$_2$—COO(CH$_2$)$_3$—]$_2$, where R=3'-tert-butyl-4'-hydroxy-5'-2H-benzotriazole-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4, 4'-dimethoxy derivatives.

2.3. Esters of substituted and unsubstituted benzoic acids, as for example 4-tertbutylphenyl salicylate, phenyl salicylate, octylphenyl salicylate, dibenzoyl resorcinol, bis(4-tert-butylbenzoyl) resorcinol, benzoyl resorcinol, 2,4-di-tertbutylphenyl 3,5-di-tert-butyl- 4-hydroxybenzoate, hexadecyl 3,5-di-tert-butyl-4-hydroxybenzoate, octadecyl 3,5-di-tert-butyl- 4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-di-phenylacrylate, methyl α-carbomethoxycinnamate, methyl α-cyano-β-methyl-p-methoxycinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol] , such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-piperidyl)sebacate, bis(2,2,6,6-tetramethyl-piperidyl)succinate, bis(1,2,2,6,6-pentamethylpiperidyl)sebacate, bis(1,2,2,6,6-pentamethylpiperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)- 2-n-butyl-2-(2-hydroxy-3,5-di-tert-butylbenzyl)malonate, 3-n-octyl- 7,7,9,9-tetramethyl-1,3,8-triazasprio[4.5]decan-2,4-dion, bis(1-octyloxy-2,2,6,6-tetramethylpiperidyl)se bis(1-octyloxy-2,2,6,6-tetramethylpiperidyl)succinate, the condensate of N,N'-bis-(2,2,6,6-tetramethyl-4-piperidyl)hexamethylenediamine and 4-morpholino-2, 6-dichloro-1,3,5-triazine, the condensate of 2-chloro-4,6-bis(4-n-butylamino- 2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)- 1,3,5-triazine and 1,2-bis-(3-aminopropylamino)ethane, 8-acetyl-3-dodecyl-7,7,9,9-tetramethyl- 1,3,8-triazaspiro[4.5]decane-2,4-dione, 3-dodecyl-1-(2,2,6,6-tetramethyl-4-piperidyl)pyrrolidine- 2,5-dione, 3-dodecyl-1-(1,2,2,6,6-pentamethyl-4-piperidyl)pyrrolidine- 2,5-dione.

2.7. Oxamides, for example 4,4'-dioctyloxyoxanilide, 2,2'-diethoxyoxanilide, 2,2'-dioctyloxy- 5,5'-di-tert-butoxanilide, 2,2'-didodecyloxy-5,5-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)- 1,3,5-triazine, 2-(2-hydroxy-4-octyloxyphenyl)-4,6-bis(2,4-dimethylphenyl)- 1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1, 3,5-triazine, 2-(2-hydroxy- 4-octyloxyphenyl)-4,6-bis(4-methylphenyl)-1,3,5-triazine, 2-(2-hydroxy-4-dodecyloxyphenyl)- 4,6-bis(2,4-dimethylphenyl)-1,3, 5-triazine, 2-[2-hydroxy-4-(2hydroxy- 3-butyloxypropoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl )thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphsophite, tristearyl sorbitol triphosphite, tetrakis(2,4-di-tert-butylphenyl) 4,4'-biphenylene diphosphonite, 6-isooctyloxy- 2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl)methylphosphite, bis(2,4-di-tert-butyl-6-methylphenyl)ethylphosphite.

5. Hydroxylamines, for example dibenzylhydroxylamine, dioctylhydroxylamine, didodecylhydroxylamine, ditetradecylhydroxylamine, dihexadecylhydroxylamine, dioctadecylhydroxylamine, 1-hydroxy-2,2,6,6-tetramethyl-4-piperidyl benzoate or bis(1-hydroxy- 2,2,6,6-tetrameth yl-4-piperidyl)sebacate.

6. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

7. Polyamide stabilisers, for example, copper salts in combination with iodides and/or phosphorus compounds and salts of divalent manganese.

8. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or tin pyrocatecholate.

9. Nucleating agents, for example, 4-tert-butylbenzoic acid, adipic acid, diphenylacetic acid.

10. Fillers and reinforcing agents, for example, calcium carbonate, silicates, glass fibres, asbestos, talc, kaolin, mica, barium sulfate, metal oxides and hydroxides, carbon black, graphite.

11. Other additives, for example, plasticisers, lubricants, emulsifiers, pigments, optical brighteners, flameproofing agents, antistatic agents and blowing agents.

12. Benzofuranones and indolinones, for example those disclosed in U.S. Pat. No. 4,325,863, U.S. Pat. No. 4,338,244, U.S. Pat. No. 5,175,312, U.S. Pat. No. 5,216, 052, U.S. Pat. No. 5,252,643, DE-A- 4 316 611, DE-A-4 316 622, DE-A-4 316 876, EP-A-0 589 839 or EP-A-0 591 102 or 3-[4-(2-acetoxyethoxy)phenyl] -5,7-di-tert-butyl-benzofuran-2-one, 5,7-di-tert-butyl-3-[4-(2-stearoyloxyethoxy)phenyl] benzofuran-2-one, 3,3'-bis[5, 7-di-tert-butyl-3-(4-[2-hydroxyethoxy]-phenyl)benzofuran- 2-one], 5,7-di-tert-butyl-3-(4-ethoxyphenyl)benzofuran-2-one, 3-(4-acetoxy- 3,5-dimethylphenyl)-5,7-di-tert-butyl-benzofuran-2-one, 3-(3,5-dimethyl-4-pivaloyloxyphenyl)- 5,7-di-tert-butyl-benzofuran-2-one.

The compounds of the formula (I) can also be used as stabilizers, especially as light stabilizers, for almost all materials known in the art of photographic reproduction and other reproduction techniques as e.g. described in Research Disclosure 1990, 31429 (pages 474 to 480).

Several examples of the preparation and use of the compounds of the formula (I) are reported for more detailed illustration of the present invention; these examples are given solely for illustrative purposes and do not imply any restriction.

EXAMPLE 1

Preparation of tetradecyl 2,2,6,6-tetramethyl-4-piperidinyl carbonate.

27.7 g (0.1 mol) of tetradecyl chlorocarbonate are added slowly to a solution of 19.4 g (0.1 mol) of 2,2,6,6-tetramethyl-4-piperidinol hydrochloride in 150 ml of dichloromethane, maintaining the temperature at between 0° C. and 5° C. After the end of the addition, the mixture is stirred for 2 hours at ambient temperature, and a solution of 8.8 g (0.22 mol) of NaOH in 50 ml of water is then added slowly, with cooling to −10° C.

The mixture is stirred for 30 minutes and, after separating off the aqueous phase, the organic phase is dried over $Na_2SO_4$ and evaporated, and the residue is distilled in vacuo.

The product obtained has a boiling point of 195°–196° C./0.3 mbar and solidifies with melting point 27°–29° C.

Analysis for $C_{24}H_{47}NO_3$ Calculated: C=72.49%; H=11.91%; N=3.52% Found: C=72.42%; H=11.94%; N=3.49%

EXAMPLE 2

Preparation of octadecyl 2,2,6,6-tetramethyl-4-piperidinyl carbonate.

The product is prepared as described in Example 1 by reacting 33.3 g (0.1 mol) of octadecyl chlorocarbonate with 19.4 g (0.1 mol) of 2,2,6,6-tetramethyl-4-piperidinol hydrochloride in 150 ml of dichloromethane. After treatment with an aqueous solution of NaOH, the product obtained has a melting point of 54°–55° C.

Analysis for $C_{28}H_{55}NO_3$ Calculated: C=74.12%; H=12.22%; N=3.09% Found: C=73.97%; H=12.14%; N=3.10%

EXAMPLE 3

Preparation of 1,2,2,6,6-pentamethyl-4-piperidyl tetradecyl carbonate.

27.7 g (0.1 mol) of tetradecyl chlorocarbonate are added slowly to a solution of 19.3 g (0.1 mol) of the sodium salt of 1,2,2,6,6-pentamethyl-4-piperidinol in 150 ml of toluene, maintaining the temperature at 0° C. After the end of the addition, the mixture is stirred for 2 hours at ambient temperature, washed with water, dried over $Na_2SO_4$ and evaporated. The residue is distilled in vacuo. The product obtained has a boiling point of 172°–174° C./0.3 mbar and solidifies with melting point 32°–34° C.

Analysis for $C_{25}H_{49}NO_3$ Calculated: C=72.94%; H=12.00%; N=3.40% Found: C=72.91%; H=11.96%; N=3.42%

EXAMPLE 4 a) Preparation of mono(1,2,2,6,6-pentamethyl-4-piperidyl) succinate.

A solution of 68.5 g (0.4 mol) of 1,2,2,6,6-pentamethyl-4-piperidinol in 150 ml of anhydrous N,N-dimethylacetamide is added slowly to a solution, heated to 60° C., of 40 g (0.4 mol) of succinic anhydride in 50 ml of anhydrous N,N-dimethylacetamide. After the end of the addition, the mixture is heated for 2 hours at 110° C., the solvent is evaporated and the residue is crystallized from acetonitrile. The product obtained melts at 163°–165° C.

b) Preparation of octyl 1,2,2,6,6-pentamethyl-4-piperidyl succinate.

A mixture of 35.3 g (0.13 mol) of mono(1,2,2,6,6-pentamethyl-4-piperidyl) succinate, 25.1 g (0.13 mol) of 1-bromooctane and 13.2 g (0.13 mol) of triethylamine in 70 ml of anhydrous N,N-dimethylacetamide is heated for 4 hours at 85° C. After cooling to ambient temperature, 200 ml of water and 150 ml of toluene are added and a solution of 18 g (0.13 mol) of $K_2CO_3$ in 50 ml of water is then added slowly. After the end of the addition, the mixture is stirred for 15 minutes, the aqueous phase is separated off and the organic phase is washed with water until neutral and evaporated. The residue is distilled in vacuo. The product obtained has a boiling of 170° C./4 mbar.

Analysis for $C_{22}H_{41}NO_4$ Calculated: C=68.89%; H=10.77%; N=3.65% Found: C=68.20%; H=10.74%; N=3.61%

EXAMPLE 5 a) Preparation of mono(2,2,6,6-tetramethyl-4-piperidyl) succinate.

62.9 g (0.4 mol) of 2,2,6,6-tetramethyl-4-piperidinol are added slowly to a solution, heated to 60° C., of 40 g (0.4 mol) of succinic anhydride in 200 ml of anhydrous N-methyl-2-pyrrolidinone. The mixture is stirred for 1 hour at 60° C. and then allowed to cool to ambient temperature. The precipitate which has formed is separated off by filtration, washed with a little N-methyl-2-pyrrolidinone and then with warm ethanol and finally dried in vacuo. The product obtained melts at 263°–265° C.

b) Preparation of dodecyl 2,2,6,6-tetramethyl-4-piperidyl succinate.

The product is prepared as described in Example 4b by reacting 30.9 g (0.12 mol) of mono(2,2,6,6-tetramethyl-4-piperidyl) succinate with 29.9 g (0.12 mol) of 1-bromododecane in the presence of 12.1 g (0.12 mol) of triethylamine. The product obtained has a boiling point of 195° C./5.3 mbar.

Analysis for $C_{25}H_{47}NO_4$ Calculated: C=70.54%; H=11.13%; N=3.29% Found: C=70.10%; H=11.07%; N=3.26%

EXAMPLE 6

Preparation of dodecyl 1,2,2,6,6-pentamethyl-4-piperidyl succinate.

The product is prepared as described in Example 4b by reacting 27.1 g (0.1 mol) of mono(1,2,2,6,6-pentamethyl-4-piperidyl) succinate with 24.9 g (0.1 mol) of 1-bromododecane in the presence of 10.1 g (0.1 mol) of triethylamine. The product has a boiling point of 190° C./4 mbar.

Analysis for $C_{26}H_{49}NO_4$ Calculated: C=71.03%; H=11.23%; N=3.19% Found: C=70.65%; H=11.17%; N=3.16%

EXAMPLE 7

Preparation of octadecyl 1,2,2,6,6-pentamethyl-4-piperidyl succinate.

The product is prepared as described in Example 4b by reacting 27.1 g (0.1 mol) of mono(1,2,2,6,6-pentamethyl-4-piperidyl) succinate with 33.3 g (0.1 mol) of 1-bromooctadecane in the presence of 10.1 g (0.1 mol) of triethylamine. The product obtained has a melting point of 38°–40° C. after crystallization from acetonitrile.

Analysis for $C_{32}H_{61}NO_4$ Calculated: C=73.37%; H=11.74%; N=2.67% Found: C=73.30%; H=11.63%; N=2.64%

EXAMPLE 8

Light-stabilizing action in polypropylene plaques.

1 g of each of the compounds indicated in Table 1, 1 g of tris (2,4-di-t-butylphenyl)phosphite, 0.5 g of pentaerythritol tetrakis[3-(3,5-di-t-butyl-4-hydroxyphenyl)propionate], 1 g of calcium stearate and 1 g of Filofin Blue G are mixed in a turbo mixer with 1000 g of polypropylene powder of melt index=4 g/10 minutes (measured at 230° C. and 2.16 kg). The mixtures obtained are extruded at a temperature of 200°–230° C. to give polymer granules which are then convened into plaques of 2 mm thickness by injection moulding at 200°–220° C. The plaques obtained am exposed in a model 65 Wr Weather-O-Meter (ASTM D2565-85) with a black panel temperature of 63° C. until surface embrittlement (chalking) starts. A plaque of polypropylene prepared under the same conditions as indicated above but without the addition of the compounds of the invention is exposed for comparison. In Table 1, the exposure tinge needed to reach this start of embrittlement is given in hours. The longer the time the better is the stabilizing effect.

TABLE 1

| Stabilizer | Chalking time (hours) |
|---|---|
| None | 570 |
| Product of Example 1 | 4900 |
| Product of Example 2 | 4680 |
| Product of Example 4 | 4400 |

What is claimed is:
1. A compound of the formula (I)

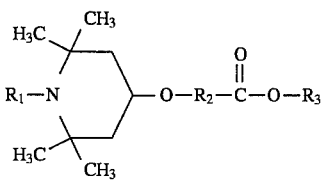 (I)

in which $R_1$ is hydrogen, $C_1$–$C_8$alkyl, O·, OH, $CH_2CN$, $C_1$–$C_{18}$alkoxy, $C_5$–$C_{12}$ cycloalkoxy, $C_3$–$C_6$alkenyl $C_7$–$C_9$phenylalkyl unsubstituted or mono-, di- or tri-substituted on the phenyl by $C_1$–$C_4$alkyl or $R_1$ is aliphatic $C_1$–$C_8$acyl;

$R_2$ is a direct bond, methylene, carbonyl or a group

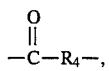

the group $R_4$ being bound to the group

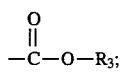

$R_3$ is $C_5$–$C_{18}$alkyl, $C_3$–$C_{18}$alkenyl, $C_5$–$C_{12}$ cycloalkyl unsubstituted or mono-, di- or tri-substituted by $C_1$–$C_4$alkyl, or $R_3$ is $C_7$–$C_9$phenylalkyl which is mono-, di- or tri-substituted on the phenyl by $C_1$–$C_4$alkyl;

$R_4$ is linear $C_1$–$C_4$alkylene, a group

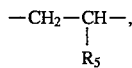

a group

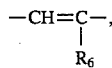

$C_2$–$C_4$oxaalkylene, $C_5$–$C_7$cycloalkyl-1,2-ene or $C_5$–$C_7$cycloalken-1,2-ylene;

$R_5$ is $C_1$–$C_{18}$alkyl or $C_3$–$C_{18}$alkenyl; and $R_6$ is hydrogen or $C_1$–$C_4$alkyl, with the proviso that, when $R_1$ is hydrogen and $R_3$ is —$C_{16}H_{33}$, $R_2$ is not a direct bond or a carbonyl group.

2. A compound of the formula (I) according to claim 1, in which $R_1$ is hydrogen, $C_1$–$C_4$alkyl, OH, $C_6$–$C_{12}$alkoxy, $C_5$–$C_8$cycloalkoxy, allyl, benzyl or acetyl.

3. A compound of the formula (I) according to claim 1, in which $R_2$ is a direct bond, methylene, carbonyl, a group

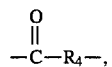

$R_3$ is $C_5$–$C_{18}$alkyl, $C_5$–$C_{18}$alkenyl, $C_5$–$C_8$cycloalkyl unsubstituted or mono-, di- or tri-substituted by $C_1$–$C_4$alkyl; or benzyl mono-, di- or tri-substituted on the phenyl by $C_1$–$C_4$alkyl, $R_4$ is linear $C_1$–$C_3$alkylene, a group

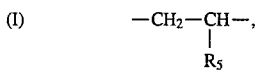

a group

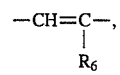

$C_2$–$C_4$oxaalkylene, $C_6$–$C_7$cycloalkyl-1,2-ene, or $C_6$–$C_7$cycloalken-1,2-ylene, $R_5$ is methyl, $C_3$–$C_{18}$alkyl or $C_3$–$C_{18}$alkenyl, and $R_6$ is hydrogen or $C_1$–$C_2$alkyl.

4. A compound of the formula (I) according to claim 1, in which $R_2$ is a direct bond, methylene, carbonyl or a group

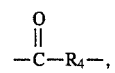

$R_3$ is $C_6$–$C_{18}$alkyl, $C_6$–$C_{18}$alkenyl, cyclohexyl unsubstituted or mono-, di- or tri-substituted by $C_1$–$C_4$alkyl; or benzyl mono-, di- or tri-substituted on the phenyl by $C_1$–$C_4$alkyl, $R_4$ is ethylene, trimethylene, a group

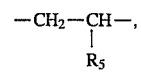

a group

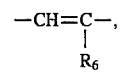

a group —$CH_2$—O—$CH_2$—, 1,2-cyclohexylene, 4-methyl-1,2-cyclohexylene, 4-cyclohexen-1,2-ylene, or methyl-4-cyclohexen-1,2-ylene or $R_5$ is methyl, $C_4$–$C_{18}$alkyl or $C_4$–$C_{18}$alkenyl, and $R_6$ is hydrogen or methyl.

5. A compound of the formula (I) according to claim 1, in which $R_2$ is a direct bond, methylene or a group

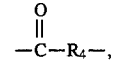

$R_3$ is $C_8$–$C_{18}$alkyl, undecenyl, or octadecenyl, cyclohexyl $R_4$ is ethylene, trimethylene, a group

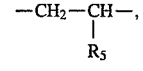

a group —CH=CH—, a group —$CH_2$—O—$CH_2$—, 1,2-cyclohexylene or 4-methyl-1,2-cyclohexylene, and $R_5$ is methyl, $C_4$–$C_{12}$alkyl or $C_4$–$C_{12}$alkenyl.

6. A compound of the formula (I) according to claim 1, in which $R_1$ is hydrogen or methyl, $R_2$ is a direct bond or a group

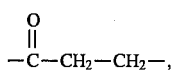

and $R_3$ is $C_8$–$C_{18}$alkyl.

7. A composition which contains an organic material susceptible to degradation induced by light, heat and oxidation and at least one compound of the formula (II)

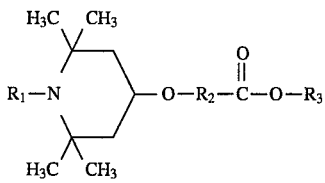

in which $R_1$ is hydrogen, $C_1$–$C_8$alkyl, O·, OH, $CH_2CN$, $C_1$–$C_{18}$alkoxy, $C_5$–$C_{12}$ cycloalkoxy, $C_3$–$C_6$alkenyl, $C_7$–$C_9$phenylalkyl unsubstituted or mono-, di- or tri-substituted on the phenyl by $C_1$–$C_4$alkyl; or aliphatic $C_1$–$C_8$acyl, $R_2$ is a direct bond, methylene, carbonyl or a group

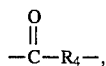

the group $R_4$ being bound to the group

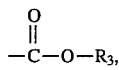

$R_3$ is $C_5$–$C_{18}$alkyl, $C_3$–$C_{18}$alkenyl, $C_5$–$C_{12}$ cycloalkyl unsubstituted or mono-, di- or tri-substituted by $C_1$–$C_4$alkyl; or $C_7$–$C_9$phenylalkyl unsubstituted or mono-, di- or tri-substituted on the phenyl by $C_1$–$C_4$alkyl, $R_4$ is linear $C_1$–$C_4$alkylene, a group

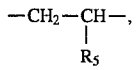

a group

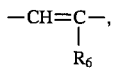

$C_2$–$C_4$oxaalkylene, $C_5$–$C_7$cycloalkyl-1,2-ene, $C_5$–$C_7$cycloalken-1,2-ylene or 1,2-phenylene, $R_5$ is $C_1$–$C_{18}$alkyl or $C_3$–$C_{18}$alkenyl, and $R_6$ is hydrogen or $C_1$–$C_4$alkyl.

8. A composition according to claim 7, wherein the organic material is a synthetic polymer.

9. A composition according to claim 8, which contains other conventional additives for synthetic polymers, in addition to the compounds of the formula (I).

10. A composition according to claim 7, wherein the organic material is a polyolefin.

11. A composition according to claim 7, wherein the organic material is polyethylene or polypropylene.

12. A process for stabilizing an organic material against degradation induced by light, heat or oxidation, characterized in that at least one compound of the formula (II) defined in claim 7 is incorporated into or applied to this material.

* * * * *